(12) United States Patent
Wedekamp

(10) Patent No.: US 6,906,337 B2
(45) Date of Patent: Jun. 14, 2005

(54) METHOD AND DEVICE FOR OPERATING A UV-RADIATION SOURCE

(75) Inventor: Horst Wedekamp, Herford (DE)

(73) Assignee: Wedeco AG Water Technology (DE)

( * ) Notice: Subject to any disclaimer, the term of this patent is extended or adjusted under 35 U.S.C. 154(b) by 124 days.

(21) Appl. No.: 10/240,617
(22) PCT Filed: Mar. 7, 2001
(86) PCT No.: PCT/EP01/02562
§ 371 (c)(1),
(2), (4) Date: Dec. 23, 2002
(87) PCT Pub. No.: WO01/75936
PCT Pub. Date: Oct. 11, 2001

(65) Prior Publication Data
US 2004/0113102 A1 Jun. 17, 2004

(30) Foreign Application Priority Data
Mar. 30, 2000 (DE) .......................................... 100 15 527

(51) Int. Cl.$^7$ ................................................. G01J 1/00
(52) U.S. Cl. .................................................. 250/504 R
(58) Field of Search ........................... 250/504 R, 373, 250/435, 436; 210/748, 188, 199

(56) References Cited

U.S. PATENT DOCUMENTS

| | | | |
|---|---|---|---|
| 4,642,219 A | 2/1987 | Takata et al. | |
| 4,645,343 A | 2/1987 | Stockdale et al. | |
| 4,897,789 A | 1/1990 | King et al. | |
| 5,230,792 A | 7/1993 | Sauska et al. | |
| 5,583,819 A | * 12/1996 | Roesner et al. | 340/10.51 |
| 6,617,963 B1 | * 9/2003 | Watters et al. | 340/10.41 |

FOREIGN PATENT DOCUMENTS

| | | |
|---|---|---|
| DE | 19530485 | 2/1997 |
| DE | 19640625 | 4/1998 |
| DE | 4133614 | 10/1998 |
| DE | 198 21 797 C1 | 7/1999 |
| EP | 0 721 996 A1 | 7/1996 |
| EP | 0833548 | 4/1998 |
| FR | 2 636 076 A1 | 3/1990 |
| FR | 2 645 544 A1 | 10/1990 |
| JP | 06 010097 A | 1/1994 |
| WO | WO 99/66092 | 12/1999 |
| WO | WO/0078678 | 12/2000 |

OTHER PUBLICATIONS

Patent Abstracts of Japan, JP 61085762.
Patent Abstracts of Japan, JP 61085761.

* cited by examiner

Primary Examiner—John R. Lee
Assistant Examiner—Johnnie L Smith, II
(74) Attorney, Agent, or Firm—Robert W. Becker & Associates; Robert W. Becker

(57) ABSTRACT

The invention relates to a method for operating a UV radiation source of the low-pressure gas discharge type. Said method comprises the following steps:—impingement of at least one heating coil with a heating voltage until the temperature of said coil has been increased;—impingement of the heating coil with a starting voltage in order to induce a gas discharge;—maintenance of the gas discharge by the application of a maintaining voltage and the disconnection of the heating voltage after the gas discharge has been started; in addition the following steps are preferably executed at any point in the method;—interrogation of an identification means that is connected to the UV radiation source and—if the response to the interrogation is negative, prevention or interruption of the operation,—if the response to the interrogation is positive, authorization of the operation. The invention also relates to a UV radiation source comprising a base body (20) and at least one connection zone which bears a number of electric connections (24, 25; 26, 27), whereby an identification means (28) that can be interrogated electrically is connected to the base body (20); and to a UV disinfection facility for fluids, in particular for water or waste water, said facility comprising at least one UV radiation source and an electric control and supply circuit that is located at a distance from the radiation source, whereby the control and supply circuit comprises an interrogation means which is suitable for verifying the presence of an identification means which is optionally assigned to the UV radiation source(s).

16 Claims, 2 Drawing Sheets

METHOD AND DEVICE FOR OPERATING A UV-RADIATION SOURCE

The specification incorporates by reference the disclosure of German priority document 100 15 527.8 filed 30 Mar. 2000 and International priority document PCT/EP01/02562 filed 7 Mar. 2001.

The present invention is, of course, no way restricted to the specific disclosure of the specification and drawings, byt also encompasses any modifications within the scope of the appended claims.

BACKGROUND OF THE INVENTION

The present invention relates to a method for operating a UV radiation source, a UV radiation source itself as well as a UV disinfection facility for fluids with a radiation source.

These kinds of method and devices have been known in practice for a long time. In many cases so-called low-pressure mercury lamps are used as the UV radiation source, which with a high degree of efficiency emit UV light of a wavelength which is suitable for destroying microorganisms in fluids. In this way effluent is disinfected without using chemicals within the presently valid limits, whereby the degree of disinfection is a function of the UV dose applied.

In particular with regard to compliance with applicable legal limits for lamp operation, in practice there is a problem that, firstly, the working efficiency of the deployed lamps degrades the longer such lamps are in operation and, as a consequence thereof, such lamps must be replaced after the expiration of a given operating time. Secondly, the operational characteristics of a UV disinfection facility can be disadvantageously altered if the lamps which are no longer usable are replaced by third party manufacturer—sourced radiation lamps which are not suitable with respect to their power or work efficiency rating to produce the requisite high radiation power over the predicted operating life.

SUMMARY OF THE INVENTION

It is, therefore, the object of the present invention to provide a method, a UV radiation source, as well as a UV disinfection facility in connection with which the commencement of operation of the disinfection facility with a lamp which is not sourced from an authorized manufacturer cannot be undertaken without effort beyond the normal lamp installation effort. In a further embodiment of the invention, each individual radiation source is to be individually identifiable and, to the extent possible, is to be identified with the actually incurred operating hours.

Due to the fact that selected locations are supplemented with an identification means connected to the UV radiation source, and upon interrogation, if the response to the interrogation is negative, the operation is prevented or interrupted, and if the response to the interrogation is positive, authorization for the operation is given, a facility can only be started up if the identification means is present and is operating to identify the radiation source as an approved radiation source.

Due to the fact that an identification means which can be interrogated electronically is connected to the base body, a control correspondingly oriented for performing an interrogation of the identification means can interrogate this identification means. Only a UV radiation source having been provided with this identification means from an approved manufacturer and for this reason deemed authorized can then be recognized as authorized by a correspondingly oriented control.

Due to the fact that the control and supply circuit has an interrogation means, which is suitable for verifying the presence of one of the at least one identification means, which has been selectively configured as a UV radiation source, the UV disinfection facility can request information concerning the type and, therefore, the properties of the UV radiation source as well as, as desired, the condition of the UV radiation source and thereby make possible the commencement of operation of the interrogated UV radiation source with the origin of the UV radiation source being the decision criterion for the commencement or not of the operation. In this manner, the commencement of operation of non-authorized radiation sources can be prevented.

In accordance with further details of the method of the present invention, it can be additionally provided that the interrogation step is performed before the impingement of the radiation source with a starting voltage and, preferably, also before the impingement thereof as well with a heating voltage. It can be provided that the identification means contains information about the manufacturer and/or the type of the radiation source and, in this way not only the origin, but, as well, the power, the emission characteristic, etc. can be established. If in addition to this, the identification means also comprises information individually identifying the radiation source by way of a serial number, the use and operation of each such individually identified radiation source can be monitored throughout its operational life.

The identification means can have a read-write memory which contains information concerning the cumulative operating life of the radiation source. In this manner, the actual number of operating hours of a radiation source can be recorded and, indeed, can be recorded even if the respective radiation source has been removed from a disinfection facility before reaching its maximum operating life and thereafter re-inserted. Lack of certainty or ambiguity regarding the age of the radiation source cannot, therefore, arise.

If the radiation source, in accordance with the present invention, is further provided with identification means connected to the base body in such a manner that a release of the identification means from the base body would effect destruction of the identification means, deliberate unauthorized manipulation of the light source is also not possible. The identification means can, moreover, be an electronic circuit which is connected by the electrical connections and, in this way, can be electrically evaluated. In this connection, the identification means can have two electrical connections and be electrically connected in parallel to a heating coil. The identification means can also have three (or more) electrical connections, two of which are electrically connected in parallel to a heating coil and at least a third connection provided for data transmission.

The identification means can alternatively be configured as a transponder, which conventionally receives and transmits in a wireless manner and which identifies the radiation source depending upon the return answer of the radiation source to an interrogation thereof.

Due to the fact that the UV disinfection facility is further outfitted such that the interrogation means is associated with an electronic starting device, a data transmission can be effected directly via the connecting wires of the UV radiation source. In this manner, the interrogation means provided in the UV disinfection facility can be connected via a 2-wire lead to the identification means assigned to the UV radiation source. The interrogation means can preferably exchange data in the form of signals with the identification means, which are modulated in correspondence with a heating voltage of a heating coil. In this manner, the number of electrical connecting wires required for connection between the control and the UV radiation source is minimized.

BRIEF DESCRIPTION OF THE DRAWINGS

Exemplary embodiments of the present invention are described below with reference to the drawings, wherein.

DESCRIPTION OF PREFERRED EMBODIMENTS

Figure 1:
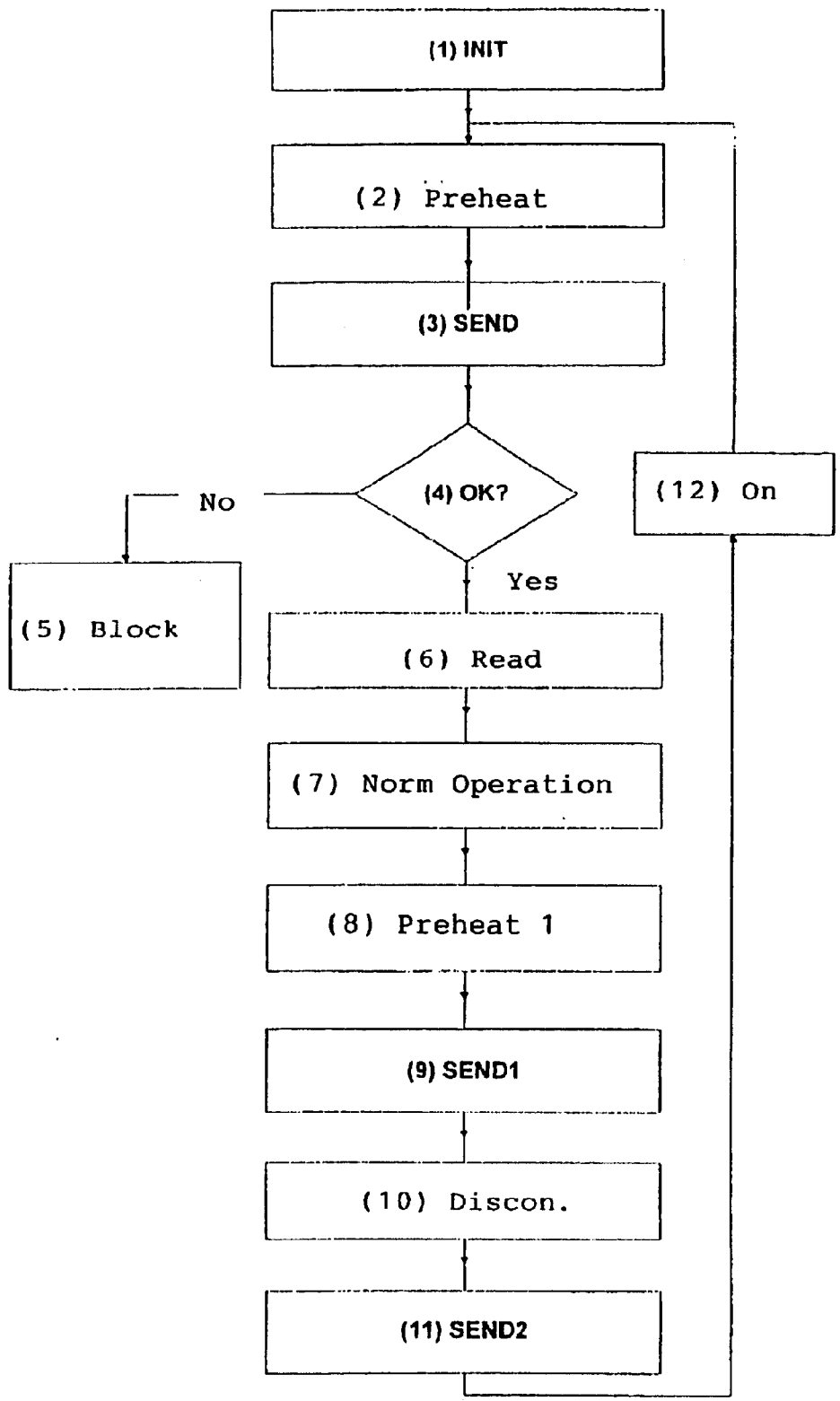
FIG. 1: A flow chart of a method according to the invention, in which an identification process is undertaken before the radiation source is activated.

In FIG. 1, an operational diagram shown as a flow chart illustrates the method of the present invention. This flow chart describes a variation of the method which is intended for UV lamps in which the identification means is provided in the form of an electronic component extending parallel to one of the two heating coils, the control of, and receipt of information from, the identification means being accomplished via the two connecting wires which are anyway provided for the electrical supply to the heating coil.

In the first step of the method, which precedes the actual operation, the identification circuit of the factory new, not previously inserted lamp is provided in the work location with a unique code. The code contains both the identity of the manufacturer and the type of the lamp, as well as a unique serial number associated solely with the respective lamp. This code is stored in a non-volatile memory, preferably EEPROM.

In operation, that is, when the lamp is deployed in a UV disinfection facility for effluent, initially, the method step 2 is performed in which the heating coils of the UV lamp are pre-heated via impingement by a heating voltage. The heating voltage in this case serves as a supply voltage for the identification circuit, which is connected in parallel to the heating coil. If the application of the pre-heat voltage is accounted for, then, in the third step of the method, a signal operable as an interrogation sequence is modulated to correspond with the pre-heat voltage. The signal contains the interrogation information in the form of a pulse sequence. In step 4 of the method, the presence and correlation of the code with the predefined values is confirmed by means of a digital logic, which is integrated into the electronic start device of the respective lamp. If the code is not accepted, the lamp is not approved for the given UV disinfection facility or, if the code is, moreover, entirely missing, step 5 of the method is selected by the digital logic and the operational access to the facility is blocked at least with respect to this one respective lamp.

If the code received in step 4 is recognized as valid, then step 6 of the method is performed whereupon the code is stored in the electronic start device. In this manner, the lamp connected at the respective location can be identified at a later operational time via reading of the identification stored in the electronic start device without the need to repeat the interrogation process.

Then, in continuing with the performance of the method, step 7 is performed in that the starting voltage is applied to the lamp, and, after the commencement of operation of the lamp, the operation is maintained with the normal lighting voltage. After start up, the pre-heating, which was activated in step 2 of the method, is de-activated.

In regular operation, following the passage of a prescribed time in the step 8 of the method, the pre-heating is again activated when the UV radiation source is in operation, in order to feed the identification circuit with its supply voltage. In step 9, the time expired since the performance of step 7 is recorded in an operating hour counting—type device in the identification circuit. Thereafter, in step 10, the pre-heat voltage is again de-activated. Steps 8, 9 and 10 can, as desired, be repetitively executed in a prescribed cycle such as, for example, every 12 hours, so that, in the memory of the identification circuit, substantially real time current information about the operating hours of the individual lamp accumulated up to the point is stored.

If the UV disinfection facility is shut down according to schedule, the pre-heat voltage is again activated in step 11 of the method and the final number of operating hours is transmitted to the identification circuit and stored therein. Then, the entire facility is de-activated and remains so until the facility is re-activated in a step 12 of the method. The new activation cycle begins again with step 2 of the method as described herein above.

In the event that an unscheduled facility shut down occurs, during, for example, a power failure occurring after step 10, the identification circuit will contain substantially real time current information about the operating hours. The age of this information is, at the most, as old as the most recent repeat cycle of steps 8–10.

The method described heretofore proceeds in a similar manner for the other identification circuits and identification means. In this manner, for example, a separate wire can be provided from the electronic start device to the identification means for data transmission purposes. If it is possible to omit the recording of the operating hours in the identification means, then identification can alternatively be effected in a wireless manner via a transponder, which only conveys a code without itself storing data. Also, in connection with this solution, it is ensured that, in step 4 of the method, an unapproved code will be recognized, and that the facility transitions to step 5 of the method to block the operation, if unapproved lamps are used.

In this manner, it is ensured that the UV disinfection facility cannot be operated if unapproved lamps are used, whereby the UV dose to which the effluent is exposed is below the stipulated level and, therefore, pathogenic microorganisms could possibly be released to the effluent. The method, therefore, operates to guarantee reliable operation, compliance with the prescribed limits, and, finally, protection of the environment against microbiological contamination.

Figure 2:
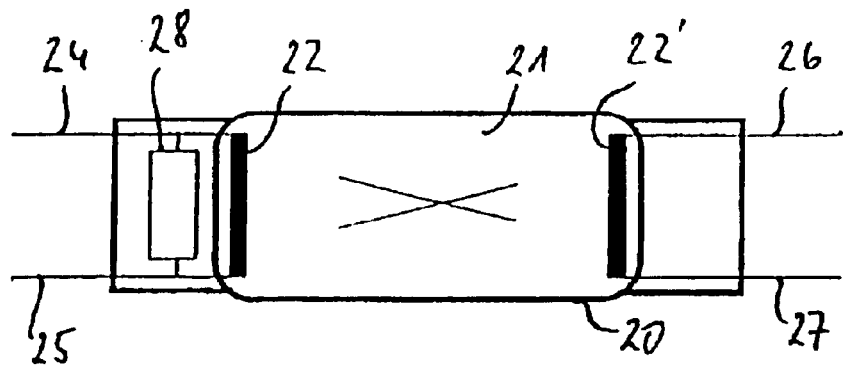
FIG. 2: A basic view of a radiation source in the form a low-pressure mercury lamp with a chip identifying it as the radiation source; as well as FIG. 3: A block diagram of an electronic starting device for use in a UV disinfection facility and for performing the method of the present invention.

In FIG. 2, a UV radiation source with an identification means configured in accordance with the present invention is diagrammatically shown. A base body 20 in the form of a gas-tight closed quartz tube forms a radiation volume 21, which contains a charge of gas as is conventionally known in connection with a low-pressure mercury lamp. A heating coil 22, 22' is arranged, respectively, on each end of the base body 20 in each configuration, the connecting wires 24, 25; 26, 27 thereof leading out from the base body. These wires normally terminate in a ceramic base (not shown) and are configured as contact pins.

An identification means 28 in the form of an integrated circuit is provided between the connecting wires 24, 25 of the heating coil 22. The integrated circuit, in this configuration, is secured to the ceramic base due to thermal and mechanical considerations and the ceramic base supports the connecting wires 24 and 25. The UV radiation source, excepting the identification circuit 28, is conventionally known. In the variation shown with the contact to identification circuit 28 effected via the connecting wires 24, 25, the UV radiation source provided with the identification means 28 remains compatible with facilities which are already in operation without the inventive circuit.

Figure 3:
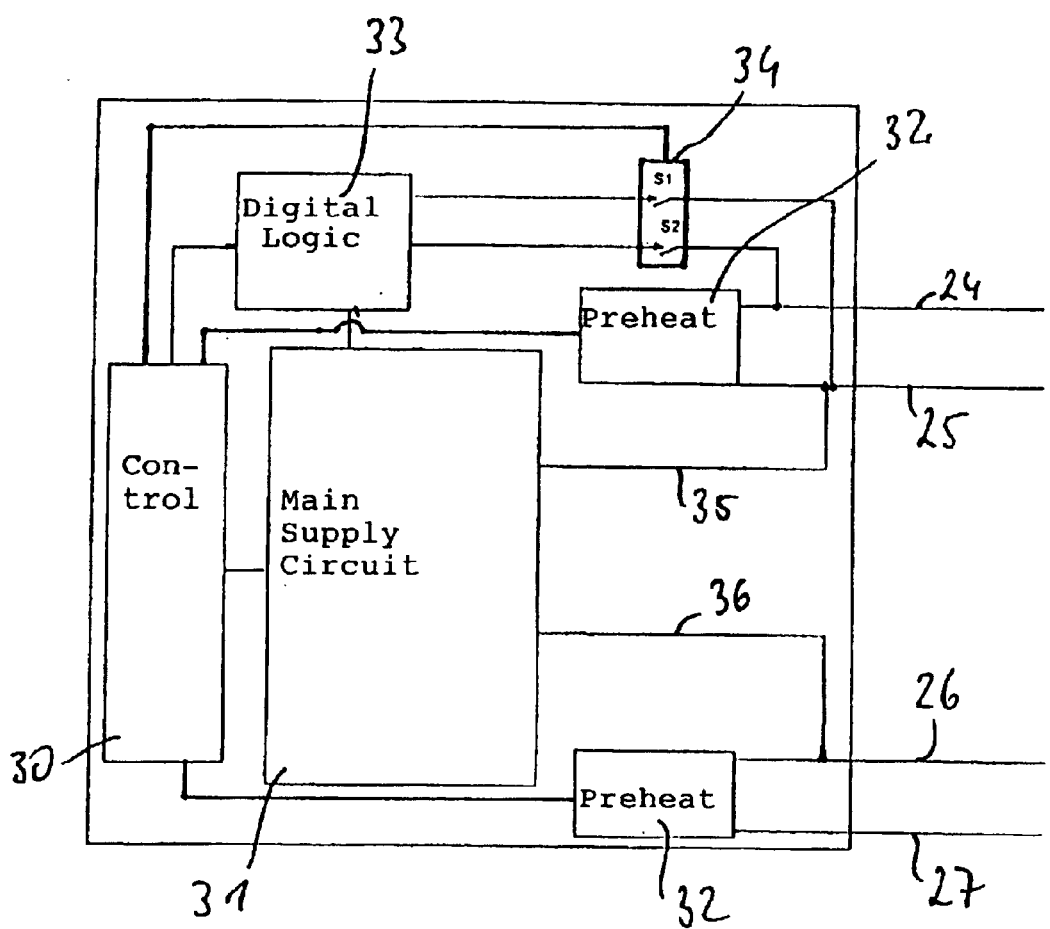

Finally, in FIG. 3, an electronic start device is shown in a block diagram, the electronic start device being suitable for operating the UV radiation source illustrated in FIG. 2 and for implementing the method as illustrated in the flow chart of FIG. 1.

The electronic start device includes a control 30, which controls a main supply circuit 31 as well as two voltage sources 32 to effect pre-heating of the heating coils 22, 22'. The control 30 also controls a digital logic 33 as well as a switch 34. *p+12X The outputs of the voltage supply 32, as illustrated in FIG. 2, are connected to the connecting wires 24, 25; 26, 27 of the radiation source.

The operation of the device is in accordance with the method described with respect to FIG. 1 in that, initially, control of the voltage source 32 is undertaken to effect the pre-heating and, thereafter, closing of the switch 34 is undertaken, so that the digital logic 33 can modulate the interrogation sequence executed via the leads 24, 25. The result of the read operation is evaluated by the digital logic 33 acting as an evaluation means and conveyed to the main supply circuit 31. If the lamp connected to the leads 24–27 is authorized to start operation, then the switch 34 is opened and the start impulse is applied via the connecting wires 35, 36 to the connecting wires 25, 26. If the radiation source is activated, then, consequently, only the maintenance voltage continues to be fed to the radiation source from the main supply circuit. The voltage supply 32 is then de-activated and is turned on again only if a new read or write operation is to be executed, as was described in detail in connection with FIG. 1.

The commencement of operation of a lamp can also be blocked by a central control in a modification of the heretofore described operation, if one of the lamps is not recognized as an authorized lamp.

What is claimed is:

1. A method for operating a UV radiation source of the low-pressure gas discharge type, the UV radiation source having a heating coil which, in response to the impingement of selected voltages thereagainst, effects the discharging of gas, the method comprising:

interrogating an identification means, the identification means being associated with the UV radiation source such that a response by the identification means to an interrogation thereof is interpretable as an identifying characteristic of the UV radiation source;

in the event that a response to the interrogation of the identification means positively correlates with information indicating that operation of the respective associated UV radiation source is authorized, permitting the operation of the UV radiation source to proceed as an authorized operation; and in the event that a response to the interrogation of the identification means does not positively correlate with information indicating that operation of the respective associated UV radiation source is authorized, intervening in connection with the operation of the respective associated UV radiation source such that at least one of a signal indicating the non-authorized status of the respective associated UV radiation source and a disablement of the operation of the respective associated UV radiation source are affected.

2. A method according to claim 1, wherein the operation of the UV radiation source includes impinging the heating coil with a starting voltage to induce a gas discharge and interrogating the identification means is performed before impinging the heating coil with a starting voltage.

3. A method according to claim 1, wherein interrogating the identification means includes interrogating an identification means containing information about at least one of the manufacturer and the type of radiation source.

4. A method according to claim 1, wherein interrogating the identification means includes interrogating an identification means containing information uniquely individually associated with the radiation source in the form of a serial number.

5. A method according to claim 1, wherein interrogating the identification means includes interrogating an identification means having a read/write memory which contains information about the accumulated operating life of the radiation source.

6. A UV radiation source, comprising:

a base body;

at least one connection area which supports a plurality of electrical connections; and an identification means which can be electrically interrogated connected to the base body.

7. A UV radiation source according to claim 6, wherein the identification means is connected to the base body in a manner such that the identification means is destroyed if it is removed from the base body.

8. A UV radiation source according to claim 6, wherein the identification means is an electronic circuit which is connected by the electrical connections.

9. A UV radiation source according to claim 6, wherein the identification means has two electrical connections and is electrically connected in parallel to a heating coil.

10. A UV radiation source according to claim 6, wherein the identification means has three electrical connections and is electrically connected in parallel to a heating coil and a third connection is provided for data transmission.

11. A UV radiation source according to claim 6, wherein the identification means is a transponder.

12. A UV disinfection facility for fluid disinfecting handling of, in particular, water or effluent, comprising:

at least one UV radiation source;

at least one identification means associated with the at least one UV radiation source; and an electrical control and supply circuit spaced from the light source, the electrical control and supply circuit including an interrogation means which is configured for verifying the presence of the at least one identification means associated with the at least one UV radiation source.

13. A UV disinfecting facility according to claim 12, and further comprising an electronic start device associated with the identification means.

14. A UV disinfecting facility according to claim 12, wherein the interrogation means is connected with the identification means via a two-wire lead.

15. A UV disinfecting facility according to claim 12, wherein the interrogation means and the identification means exchange unidirectional or bi-directional data in the form of signals, which are modulated to correlate with the voltage of a heating coil.

16. A method according to claim 1, wherein the operation of the UV radiation source includes impinging at least one heating coil with a heating voltage to effect the heating thereof up to an increased heating coil temperature, impinging the heating coil with a starting voltage to induce a gas discharge, and maintaining the discharging of gas by applying a maintenance voltage and de-activating the heating voltage after the step of impinging the heating coil with a starting voltage and interrogating an identification means is performed during a selected time before, during, or after impinging the heating coil with a heating voltage, impinging the heating coil with a starting voltage, or maintaining the discharging of the gas by applying a maintenance voltage to the heating coil.

* * * * *